United States Patent [19]
Morgan et al.

[11] Patent Number: 5,414,648
[45] Date of Patent: May 9, 1995

[54] NONDESTRUCTIVELY DETERMINING THE DIMENSIONAL CHANGES OF AN OBJECT AS A FUNCTION OF TEMPERATURE

[75] Inventors: Ira L. Morgan; Robert H. Rice; Joseph E. Bolger, all of Austin, Tex.; Donald G. Schindler, Pittsburgh, Pa.

[73] Assignee: Integrated Diagnostic Measurement Corporation, Austin, Tex.

[21] Appl. No.: 531,322

[22] Filed: May 31, 1990

[51] Int. Cl.$^6$ .............................................. G01B 15/02
[52] U.S. Cl. .................... 364/563; 250/359.1; 364/506; 364/550; 378/54
[58] Field of Search .............. 364/550, 575, 559, 560, 364/563, 506, 507; 378/4, 9, 54, 55, 58, 59; 72/8, 9, 12, 16; 250/359.1

[56] References Cited

U.S. PATENT DOCUMENTS

| | | | |
|---|---|---|---|
| 3,108,186 | 10/1963 | Flavell, Jr. | 250/65 |
| 3,109,095 | 10/1963 | Horne | 378/54 |
| 3,148,278 | 9/1964 | Schönborn et al. | 250/359.1 |
| 3,248,916 | 5/1966 | Kenyon et al. | 72/12 |
| 3,482,098 | 12/1969 | Mangan | 250/83.3 |
| 3,592,031 | 7/1971 | Sutton et al. | 72/8 |
| 3,832,549 | 8/1974 | Mangan et al. | 378/54 |
| 3,841,123 | 10/1974 | Fox et al. | 72/8 |
| 3,851,509 | 12/1974 | Fox | 72/8 |
| 3,864,573 | 2/1975 | Hoffman et al. | 250/358 |
| 3,974,248 | 8/1976 | Atkinson | 264/40.2 |
| 4,009,376 | 2/1977 | Faraguet | 364/563 |
| 4,083,002 | 4/1978 | Allport | 364/564 X |
| 4,117,732 | 10/1978 | Brazhnikov | 73/599 |
| 4,283,629 | 8/1981 | Habermehl et al. | 378/4 |
| 4,320,463 | 3/1982 | Himmelstein | 364/552 |
| 4,495,635 | 1/1985 | Dobbs | 378/54 X |
| 4,510,577 | 4/1985 | Tsujii et al. | 378/4 X |
| 4,519,041 | 5/1985 | Fant et al. | 364/552 |
| 4,695,729 | 9/1987 | Monno et al. | 378/59 X |
| 4,725,963 | 2/1988 | Taylor et al. | 364/507 |
| 4,803,639 | 2/1989 | Steele et al. | 378/4 X |
| 4,951,222 | 8/1990 | Hoffman et al. | 378/54 X |
| 5,091,862 | 2/1992 | Hoffman et al. | 250/359.1 X |

Primary Examiner—Edward R. Cosimano
Attorney, Agent, or Firm—Jerry M. Keys; Heinz D. Grether

[57] ABSTRACT

An apparatus and method for determining the shape specific contraction and expansion of cylindrical or otherwise geometrically regular-shaped products as a function of time and temperature through high precision, continuous, nondestructive dimensional analysis of a cross-section of the object as the object is heated and/or cooled. The apparatus includes multiple penetrating radiation sources and detectors. In performing the analysis on an object as its temperature changes over a certain temperature range, the apparatus generates curves or formulas representing the changes in a dimension of the object as a function of temperature and/or time.

17 Claims, 13 Drawing Sheets

NONDESTRUCTIVELY DETERMINING THE DIMENSIONAL CHANGES OF AN OBJECT AS A FUNCTION OF TEMPERATURE

RELATED APPLICATION

Pending U.S. patent application Ser. No. 07/531,454, filed concurrently herewith in the name of Morgan, et al., entitled "An Automated System for Controlling the Quality of Geometrically Regular-Shaped Products During Their Manufacture" is directed to a novel apparatus and method for automatic quality control of geometrically regular-shaped products, such as tubes and rounds over a wide range of temperatures.

BACKGROUND OF THE INVENTION

1. Field of the Invention

The present invention relates to a method of and apparatus for nondestructively determining the dimensional changes in an object as a function of temperature and, in particular, relates to an method of and apparatus for developing a dilatometry model of an object to be manufactured, wherein the model can be used by an automated quality control system to more accurately determine the dimensional quality of an object at ambient temperatures, based on a dimensional analysis of the object conducted at elevated temperatures by means of penetrating radiation and computer models of the object being examined.

2. Description of Prior Art

Historically, various means have been used to provide quality control of objects during their manufacture. In many manufacturing environments where the product being manufactured, such as tube or pipe, is actually formed at elevated temperatures, it is often desirable to initially test the product when the product is at an elevated temperature, otherwise a significant number of out-of-specification products can be produced before a defect is discovered.

In more recent manufacturing process control environments, the ability to test the product-in-manufacture at elevated temperatures is especially important if control signals are to be feedforward to additional production processes, which can correct the defect while the product remains at elevated temperatures.

In the past, quality control systems have taken measurements at elevated temperatures for the purpose of controlling the quality of the product's dimensions. For example, U.S. Pat. Nos. 3,841,123 and 3,851,509 contemplate taking temperature measurements of sheet metal as its thickness is measured by force gauges and a final X-ray gauge in order to control the manufacturing process. Likewise, U.S. Pat. No. 3,592,031 discloses an apparatus and method for correcting the manufacturing process if a measured temperature is different than the expected temperature. Finally, U.S. Pat. No. 3,248,916 contemplates another sheet metal production process control system that limits roller pressures based upon a temperature measurement.

All of the prior art systems above disclose systems that do not continuously measure the same cross-section of the object over a range of temperatures. Rather all of the disclosed inventions assume the existence of previously developed dilatometry data. Moreover, the gamma ray gauges used in the prior art devices are only accurate for measuring thickness if the density of the material is known. Since the density of the material changes with the temperature, and although the density may be calculated if the precise chemical composition of the material is known, these gauges are not useful for collecting accurate dilatometry data. Additionally, the above prior art systems only measure a single dimensional parameter of simple objects—its thickness while the present invention measures multiple parameters of complex geometrically regular objects.

Historically, dilatometry curves and data were developed for materials of a known chemical composition by various traditional techniques, such as measuring a single dimension of an object with strain gauges, laser interferometer, or other techniques as the object cooled. More recently, laser interferometers have been used to measure the change in dimensions of a sample of a product of a known chemical composition as the material cooled. This empirically developed dilatometry data, however, was limited in several respects. First, the dilatometry data for a particular product to be manufactured is usually based on empirical data developed from a sample of known chemical composition prior to the actual production run. It was impractical to sample each batch of material made in order to generate a dilatometry curve specific to each batch of material using the old measuring techniques. Secondly, it would be impractical to test these samples in an industrial environment since the prior art test requires the sample be placed in a chamber filed with inert gas. Thirdly, the prior art methods only measured one dimension of a sample at a time. The present invention measures the entire cross-sectional shape of a sample. Finally, the present invention is capable of taking measurements of a full size object at actual cooling rates and on line in real production cooling environments.

SUMMARY OF THE INVENTION

The present invention provides a new and improved method of and apparatus for nondestructively determining the dimensional changes of geometrically regular-shaped objects as a function of temperature. The novel method comprises: scanning the object with penetrating radiation, sensing the temperature of the object as it is scanned, generating electrical signals representative of the radiation attenuation as the radiation passes through the object, processing the electrical signals and density/length signals to determining dimensional measurements of the cross-section of the object at the detected temperature allowing the object to increase and/or decrease in temperature so as to take a measurement at a different temperature and periodically repeating the prior steps to obtain density/length signals at a plurality of temperatures over a desired temperature range.

BRIEF DESCRIPTION OF THE DRAWINGS

FIG. 5 is a schematic diagram of the data collection control subsystem of forming part of the apparatus of FIG. 2a.

FIG. 6 is a schematic diagram of the computer system hardware and peripherals forming part of the apparatus of FIG. 2a.

FIGS. 12a and 12a are illustrative data flow diagrams of signals originating at the source/detector as they are processed by the apparatus shown in FIG. 2a.

DESCRIPTION OF THE PREFERRED EMBODIMENT

Figure 1:
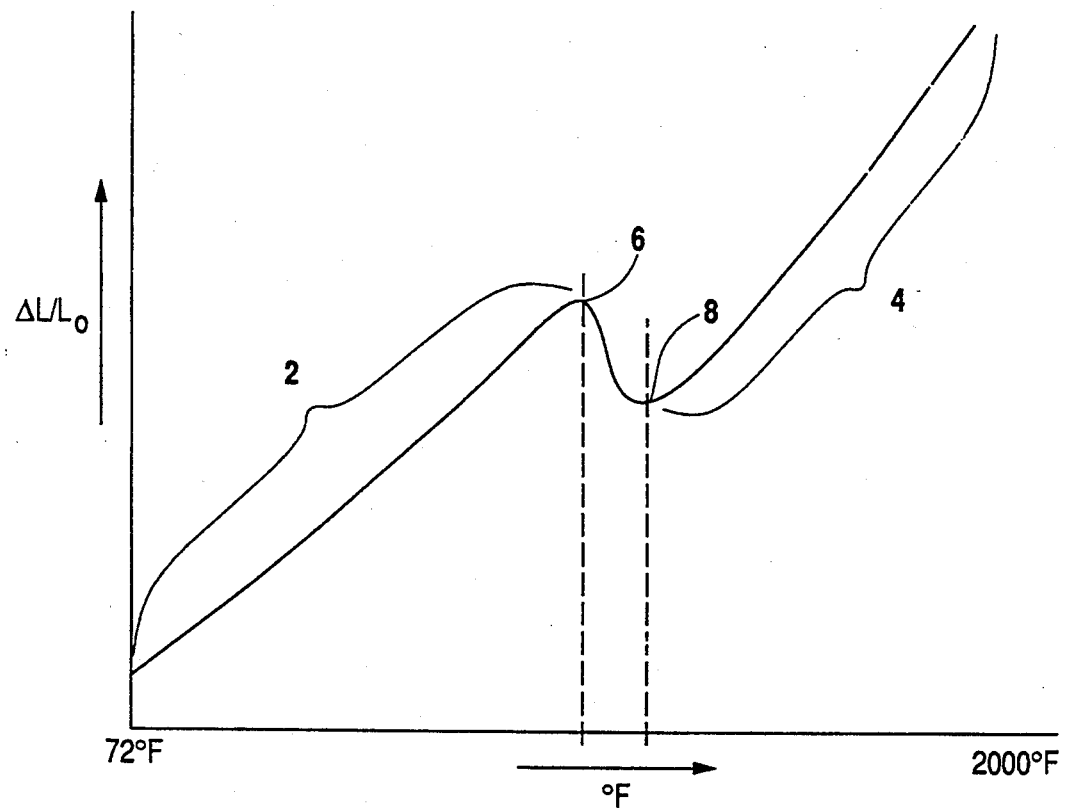
FIG. 1 is a graphic representation of a sample dilatometry curve for a carbon steel product.

FIG. 1 is a diagrammatic illustration of a typical dilatometry curve for a carbon steel product which the invention disclosed below creates. The curve shows a dimension of the object dependent on the object's temperature. The invention creates this curve by measuring a single cross-section of the object as it is heated or cooled. The invention then plots the data in a curve similar to the one shown and also performs a curve fitting operation to generate a formula that closely models the said data point curve.

The curve shown in FIG. 1 is representative of carbon steel products. The two data points 6 and 8, respectively, show the lower and upper transition points where carbon steel material changes between a ferrite/pearlite region 2 and an austenite region 4.

Historically, these curves were generated from measurements of a single dimension of a small sample in a controlled environment of inert gas. Although these techniques provided accurate results of a small sample in a controlled environment, the techniques are highly impractical for large specimens in an industrial environment.

Figure 2A:
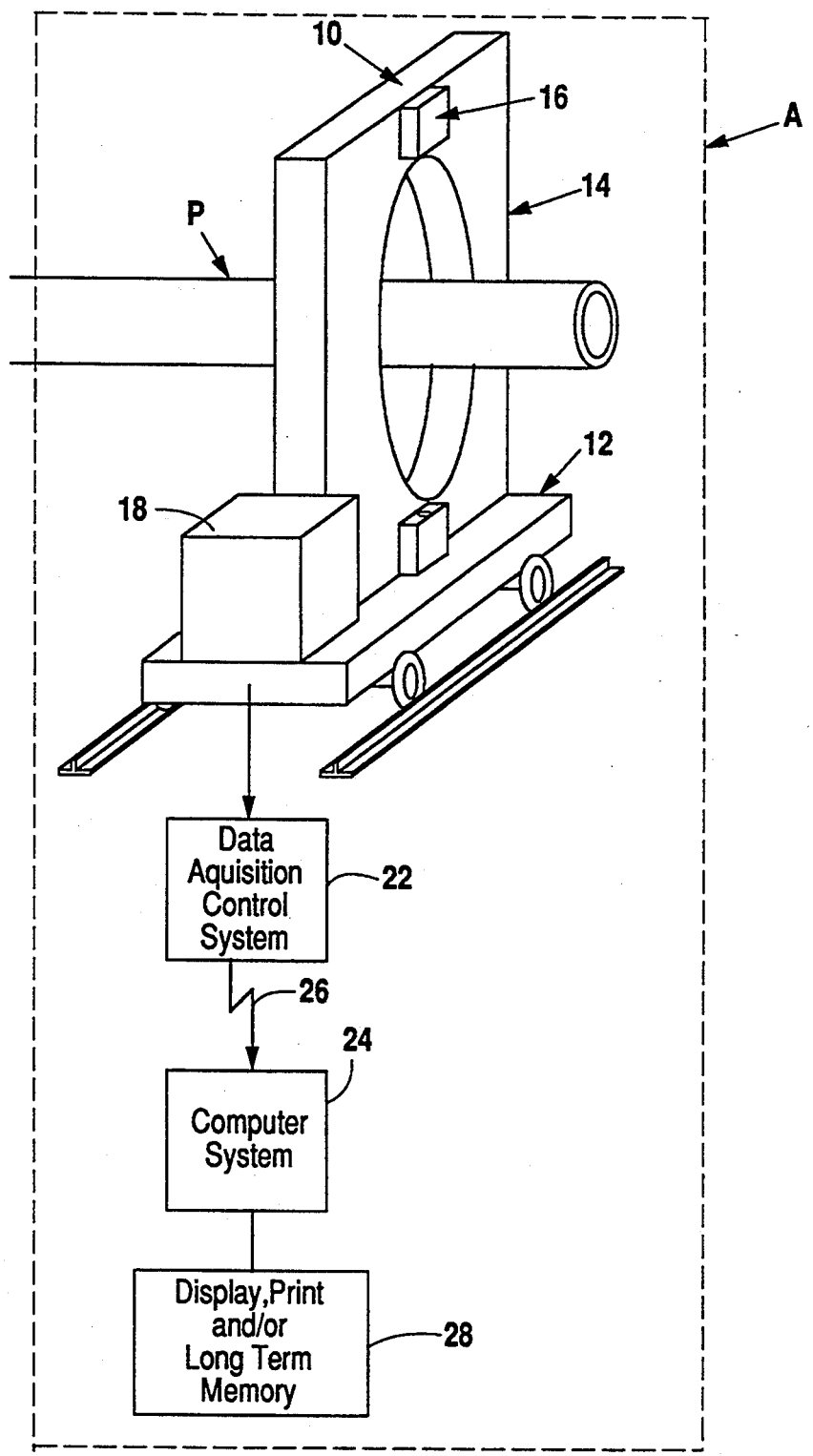
FIG. 2a is an illustrative schematic diagram of the apparatus of the present invention.

The apparatus A disclosed is not limited to steel or ferrous materials; it can be used with other materials. The apparatus and method disclosed is also not limited to cylindrical objects when modified with appropriate modeling algorithms, the method is useful with specimens of geometrically regularly-shaped objects. Hereinafter, for purposes of facilitating the descriptions, the term "tube P or product P" shall mean the billet, round tube or finished pipe P, or any other geometrically regularly-shaped object, depending on the context of the description. Tube P is used because the preferred embodiment is intended to be used in a steel tube production mill. In FIG. 2a, an illustration/schematic of the apparatus A is shown with a section of Tube P in place.

A source/detector apparatus 10, described in greater detail below, is positioned in the path of the tube P in the production line on a cart 12. Mounted to the housing 14 of the source/detector apparatus 10 is at least one, and preferably two or more, pyrometers 16 which measure the temperature of the tube P close to the source/detector apparatus 10. A suitable pyrometer for carbon steel products is a non-contact temperature transducer capable of measuring objects between 600 and 2000 degrees Fahrenheit by detecting the wavelength of the infrared radiation. The field of view of the pyrometer should be large enough to get a good average temperature of the object. Small spot sizes may show discrete differences in the measured temperature. A one inch diameter spot size should be adequate. The response time should be adjustable according to the frequency of sampling desired.

A module 18 is also mounted on the cart 12. The module 18 includes an electronics assembly for conditioning the signals from the source/detector apparatus 10, which will be described in more detail below. Electronic signals generated by the module 18 are collected by a data acquisition and control system 22. The data acquisition and control system 22 further processes the collected signals and sends the resulting information to a suitable computer system 24, via a high-speed communications link 26. Module 18 may also be incorporated within the protective housing 14.

The high-speed communications link 26 enables the computer system 24, and associated peripherals 28 discussed below, to be located remotely from any harsh environment in which the apparatus may be used. A preferred communications link 26 is a fiber optic system which would provide high-speed data transmission with minimal noise interference.

The computer system 24, described in greater detail below, processes the signals from the data acquisition control system 22 to continuously generate dimensional analysis of the cross-section of tube P and perform any additional computations.

The computer system 24 is connected to several peripherals 28, to graphically display, print and store data in permanent memory devices.

The Safety and Environmental Control System

The environment in which the apparatus A is used may be harsh and hostile to much of the equipment used with the invention. Such environments may be polluted with dirt, dust, moisture, high temperatures, vibration, noise, and electromagnetic fields.

The apparatus A of the present invention incorporates several methods of protecting components of the apparatus. The computer system 24 and its peripheral 28 are protected from any harsh environment in which the source/detector 10 is used by being located elsewhere, thus removing them from harsh environments. This is accomplished by incorporating a high-speed fiber optic communication link 26 that allows the computer system 24 and its peripheral 28 to be removed from the harsh environment, without significantly affecting the transmission time delay. An added benefit of the fiber optic communication link 26 is its virtual immunity to the high level of electromagnetic noise interference, which is commonly found in many environments. See FIG. 2a.

Figure 2B:
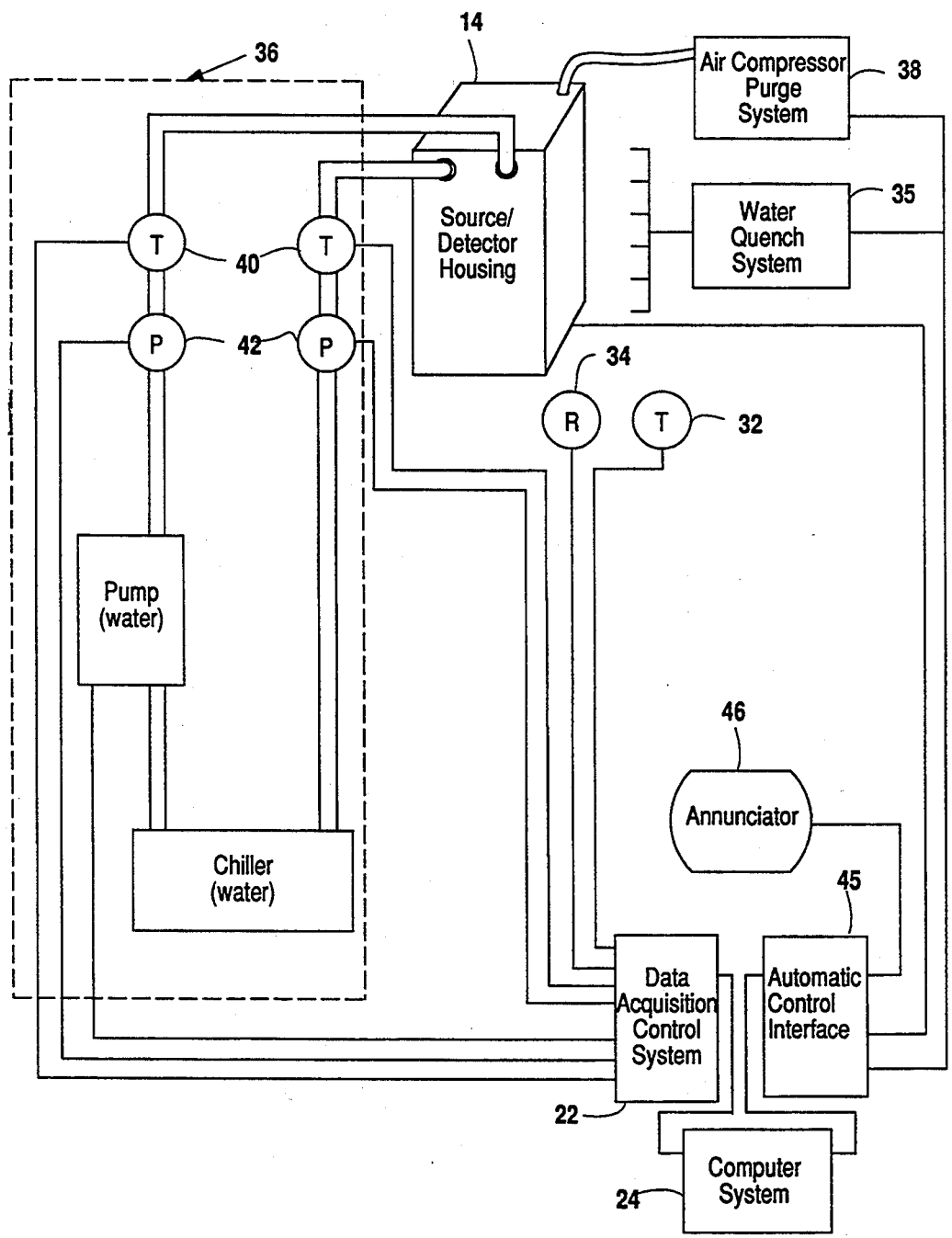
FIG. 2b is an illustrative schematic diagram of the environmental and safety control system of the apparatus.

Nevertheless, several components of the subassemblies 18 and 1 or 22 cannot be removed from the harsh environment. Accordingly, one of these components, the data acquisition control system 22, is placed in an air-tight protective enclosure. This enclosure is designed to protect the data acquisition control system 22 from dust, debris, temperature fluctuations, electromagnetic noise, vibrations and other hostile conditions. The source/detector apparatus 10 includes protective housing 14. The interior of these housings are environmentally controlled through a positive pressure air conditioning system (not shown). Slight positive pressure is used to prevent mill dirt from entering the enclosures. This positive pressure is supplied by an air coprocessor 38. See FIG. 2b.

The protective housing 14, of the source/detector apparatus 10, has additional environmental and safety features. These features are required because of heat radiating from the hot tube P that passes through the source/detector apparatus 10 and heat generated as a result of the electronic power dissipation within the housings 14 and 18. See FIG. 2b The housing 14 includes: temperature and radiation monitors inside (not shown) and outside 32 and 34 of the housing 14, a water quench system 35, which quenches the tube P if the temperature inside the housing 14 rises above a safe level, an air purge system 38 to convectionally cool the housing 14 and provide positive pressure inside the protective housings 14 and 18, a chiller system 36 with internal water temperature sensors 40, and pressure sensors 42 which circulates chilled water inside the housing 14 to protect internal components from the radiant heat from the hot tube P. If unsafe conditions are discovered, the computer 24 will send signals to an automatic control interface 45 which will sound an annunciator 46 through an annunciator 47 and shut down the source/detector apparatus 10. The safety and environmental control system is monitored and controlled by the computer system 24, as described below in the description of the main computer software.

The Source/Detector Apparatus

Figure 3:
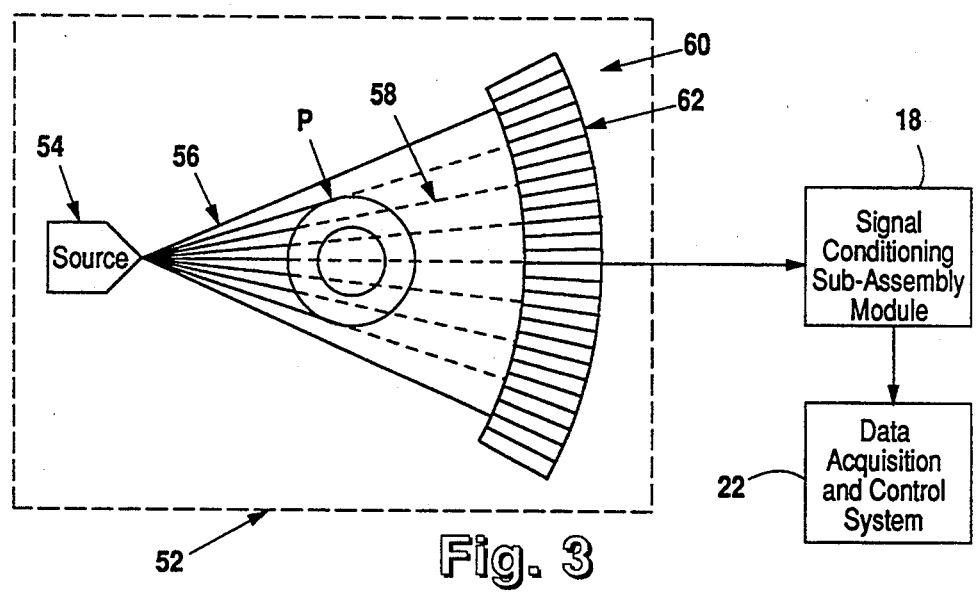
FIG. 3 is a simplified diagrammatic representation of a source/detector which forms a part of the multiple source/detector apparatus of the present invention.

FIG. 3 illustrates one source and detector array pairing 52. The source/detector apparatus 10 includes at least two of such source/detector pairs 52. In the preferred embodiment of the invention, there are three pairings 52 in the source/detector apparatus 10.

Figure 4A:
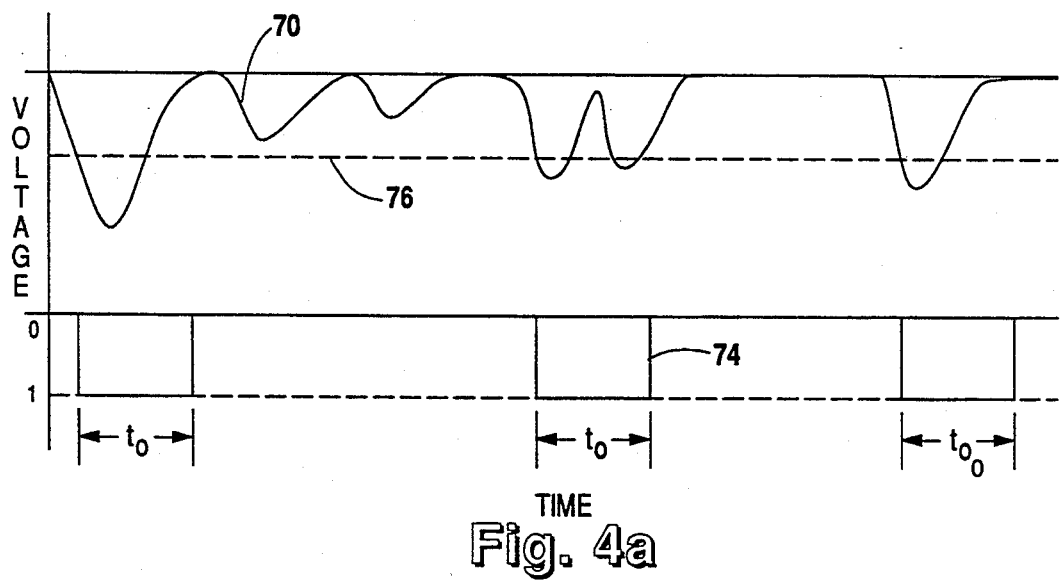
FIG. 4a is a schematic of the signal conditioning subsystem of FIGS. 2a and 3.
Figure 4B:
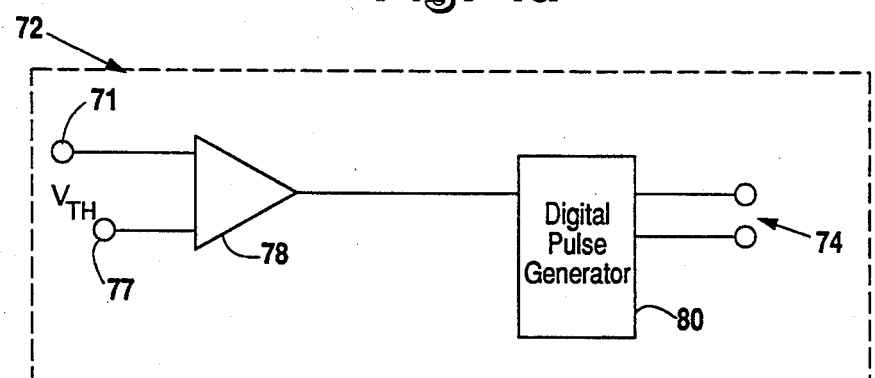
FIG. 4b is a graphic illustration of the signal generated by a detector of FIG. 3, and the converted signal generated by the signal conditioning subsystem of FIG. 4a in response to the receipt of a detector signal.

The source 54 emits a beam 56 of gamma or X-ray radiation which passes through the entire cross-section of tube P. The attenuated gamma ray or X-ray beam 58 on the opposite side of the tube P is detected by a detector array 60 which is composed of many tightly packed detectors 62. Each of the detectors 62 generate fast analog voltage signals 70, illustrated in FIG. 4a, in response to the gamma rays or X-rays detected by a detector 62. These analog signals 70 are then transmitted to multiple channel 72 of the signal conditioning module 18. A single channel 72 is shown in FIG. 4b. Since the analog signals 70 have varying amplitudes and occur randomly due to the randomly emitted photon events from a source 54, each channel 72 of module 18 is designed to generate a digital pulse or conditioned signal 74, only when the analog signal from a detector 62 has an amplitude greater than a threshold level 76. Once triggered, the channel 72 of module 18 cannot generate another conditioned signal 74 for a fixed time period $t_o$ called "dead time." The fixed dead time period allows for an accurate correction of the number of pulses counted.

Each detector 62 has slightly different recovery times in which it can recover from sensing one pulse and sensing a following pulse. This is due to the random nature of the incoming pulse height and width in the signal 70. During a detector's recovery time, additional pulses may enter the detector 62. This piling up of pulses must be corrected for. Since each detector 62 has a different recovery time, the corrections can be complicated. To simplify the correction, the circuitry sets a fixed dead time, uniform for each detector, which is greater than the largest recovery time. By using a fixed dead time, the proportion of time for which the detectors do not respond to incoming radiation is known. Knowing this proportion, the measured radiation count can be corrected to account for the total actual radiation which entered the detector. For example, if the measured radiation count was 900 and the total dead time accounted for 10% of the total time, the actual radiation count is calculated to be 1000. Using a uniform fixed dead time for all detectors allows the use of one formula for all the detectors 60; therefore, it is not necessary and is impractical to determine the response time of each individual detector.

Each channel 72 of the module 18 includes a conventional ultra-fast comparator 78 which has one input connected to the link 71 from a detector. The second input is connected to an adjustable voltage source $V_{TH}$ 77 which provides the threshold voltage 76 to the comparator. The comparator generates a trigger pulse which is then transmitted to a digital pulse generator 80. The generator 80 generates a digital pulse or conditioned signal in response to a trigger pulse at its input, but only if the trigger pulse occurs after the fixed dead time period $t_o$, as shown in FIG. 4b, prior to collection by the data acquisition control system 22. Except as described herein, suitable sources 54 and detector arrays 60 are described in U.S. Pat. No. 4,725,963.

Data Acquisition

Figure 5:
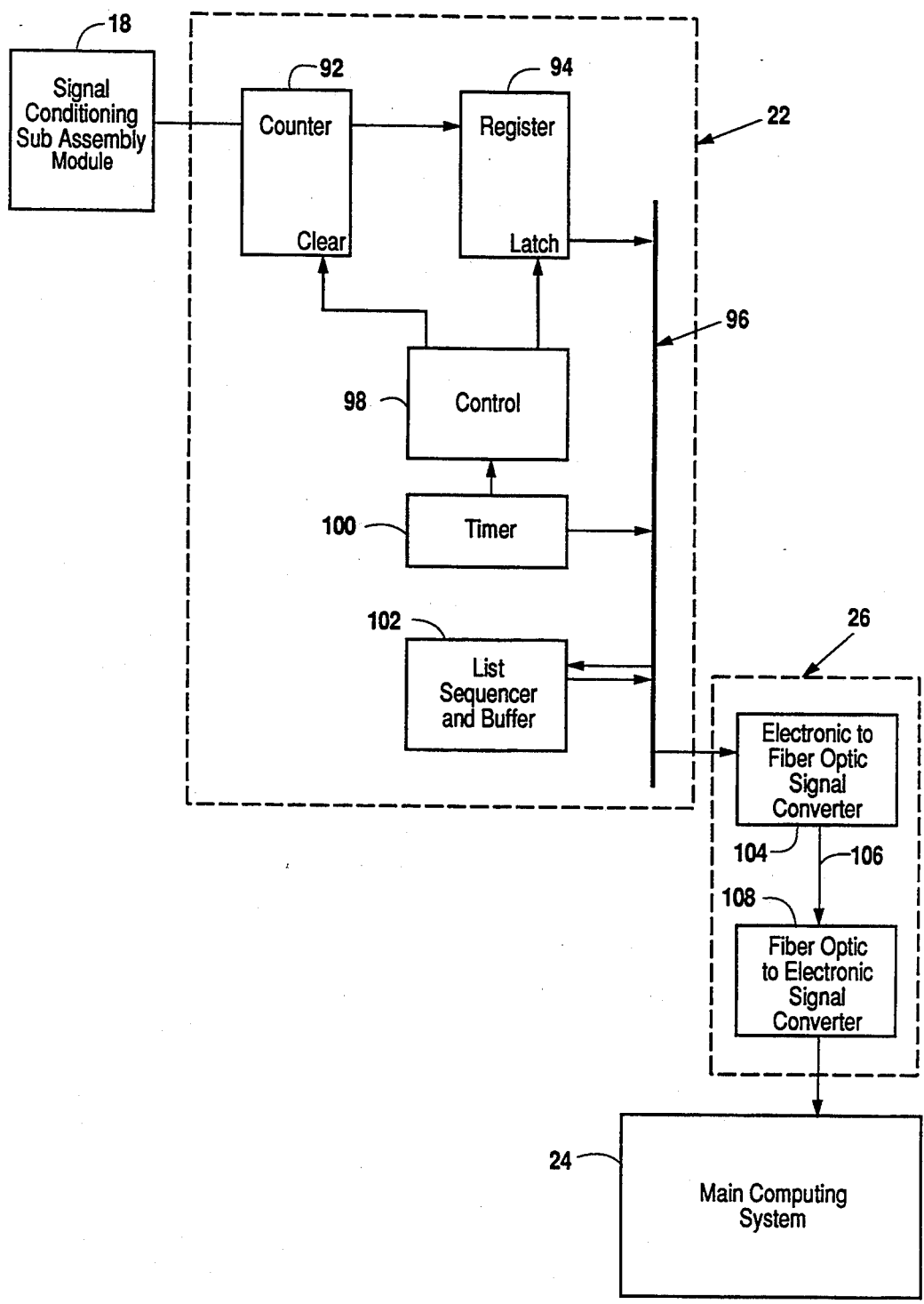

FIG. 5 provides for a more detailed description of how one channel 72 of data is collected and transmitted from the signal conditioning subassembly 18 to the computer system 24. The digital signals coming from each detector conditioning channel 74 is transmitted to a conventional counter 92, which continuously counts the number of times the signals exceed a predetermined threshold value. A data register 94 periodically latches onto the count in the counter 92 at a predetermined sampling rate and transmits the count to the data acquisition subsystem data bus 96. Immediately after the register 94 latches onto the count, the counter 92 is cleared and continues counting from zero. The latching of the register 94 and clearing of the counter 92 is effectuated by a conventional controller 98. The controller 98 has, at its disposal, a timer 100 which transmits time information to the controller 98 and the data bus 96. A suitable list sequencer and buffer 102 collects data sent from the data register 94 and blocks the data in compact format before sending the data to the computer system 24, via a suitable high-speed communication link 26 capable of transmitting 32 bit words at a rate up to 5 megabytes per second. A suitable high-speed communications link 26 is a fiber optic connection with 100 micrometer optical fiber core with attenuation of 5 dB/Km or less. An electronic-to-fiber optic signal converter 104 converts the digital signal into light pulses transmitted along a fiber optic cable 106. On the other end of the cable 106, the optical signals are reconverted into a digital signal by a fiber optic to electronic signal converter 108 which transmits the digital electronic signal to the computer system 24.

Computer Processing

Figure 6:
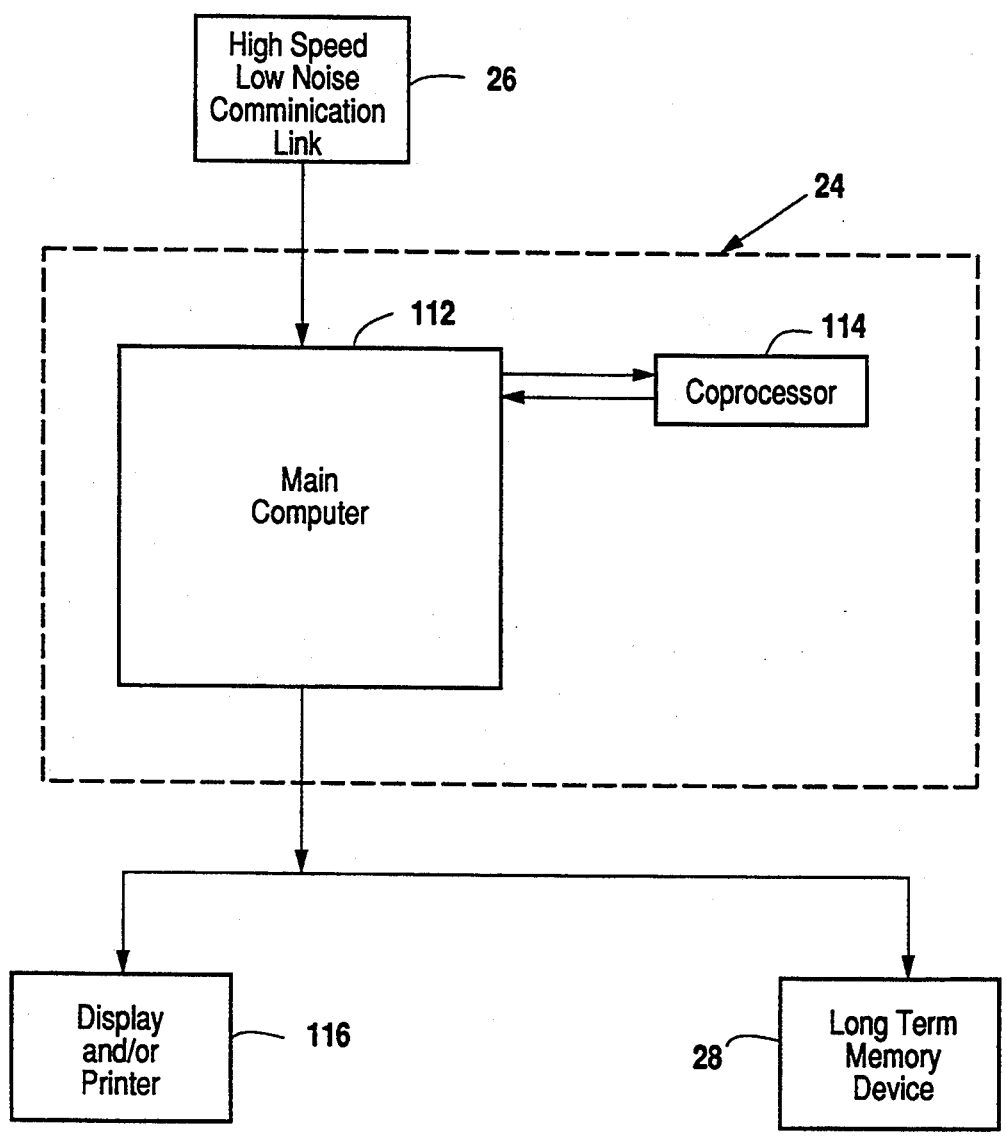

The hardware structure of the computer system 24 is illustrated in FIG. 6. The computer system 24 obtains data from the data acquisition and control system 22 through a high-speed, low noise communication link 26. Preferably, the computer system 24 is comprised of a main computer 112, with one peripheral coprocessor 114. A suitable main computer is a Digital Equipment Corporation (DEC), MicroVax II with at least 4 megabytes of main memory and a processing rate of approximately 0.9 MIPS. An array processor with a processing data rate of 20 million floating point instructions per second is a suitable coprocessor.

The computer 112 is programmed to act as the central data processing unit which assigns specific data processing tasks to the coprocessor 114 and performs the balance of the data processing itself. The computer 112 also serves as the operator's link to the other components of the apparatus A.

The general purpose of the coprocessor is to increase the effective processing data rate of the computer system 24 through parallel processing. Since the present invention was developed to be used in a steel rolling mill, getting results quickly is of significant importance.

The coprocessor increases processing speed by relieving the main computer of specific data processing tasks and performing those tasks in parallel while the computer 112 performs other tasks. For example, coprocessor 114 computes the path length of the radiation through the tube and performs analytical data reduction, described hereinafter, to determine the data points that will be used by other programs to reach a final result, while the computer continues to collect data and perform other calculations. The data processing tasks performed by coprocessor 114 will be disclosed in greater detail below.

Alternatively, the DEC MicroVax and coprocessor could be replaced by any other computer system capable of interfacing to the required peripherals and data acquisition electronics and which has a total processing rate equal to or exceeding the MicroVax and its coprocessors.

As another alternative, there is no urgency for the results then speed is not a factor and a coprocessor is not necessary. As the data is collected, it could be placed in a peripheral memory device and then later retrieved for processing at the computer's leisure.

The computer system 24 is also connected to numerous peripherals 28 and 116, which can display or print information and also store or archive data in electronic long term memory devices.

Main Computer Software

Figure 7:
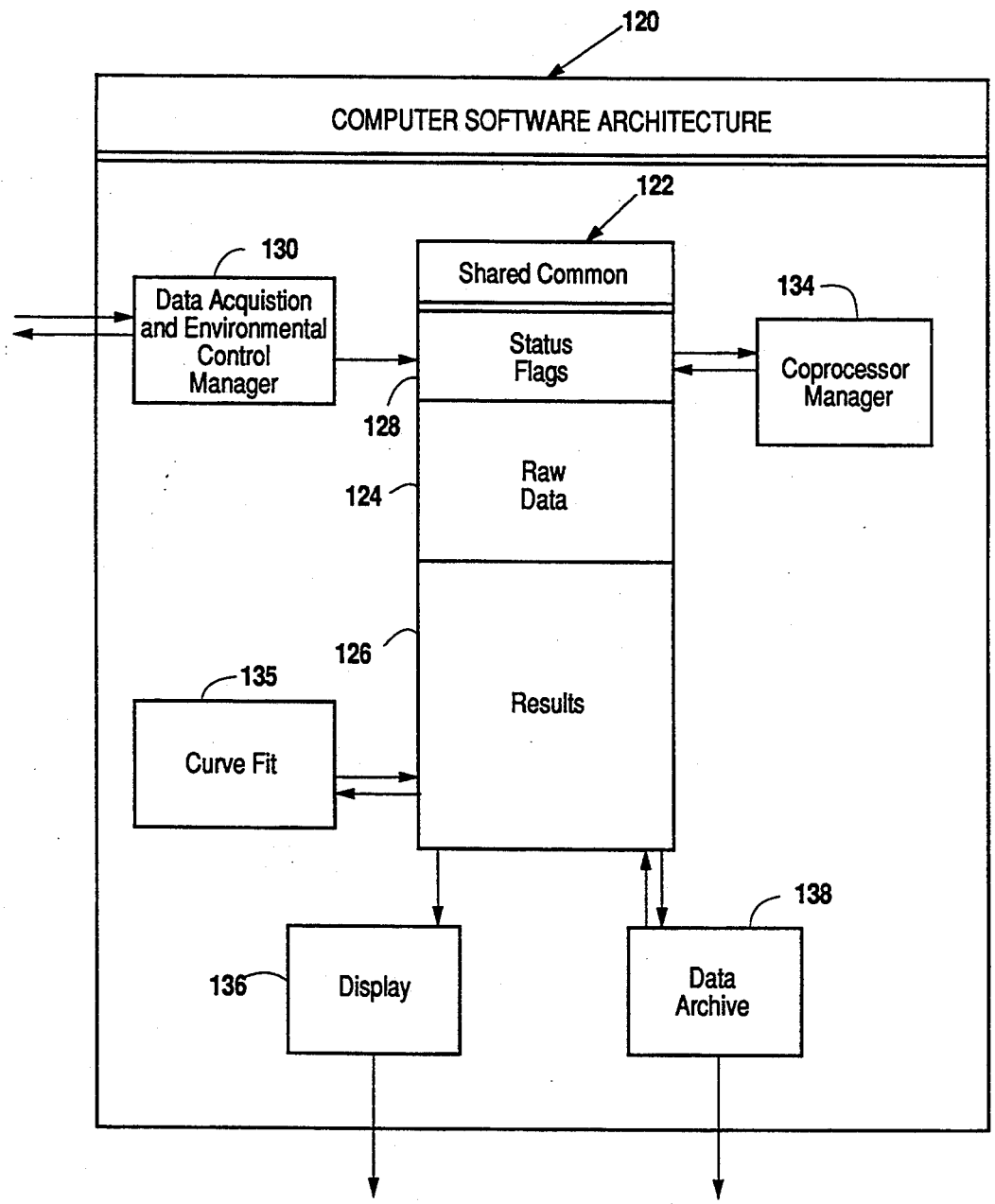
FIG. 7 is a diagrammatic illustration of the software architecture of the main computer system shown in FIG. 6.

The application software architecture 120 of the main computer 112 is illustrated in FIG. 7. The software architecture 120 is centered around shared common memory 122, which is a partitioned section of the main memory of the computer 112 which makes data available to the various programs described herein, which need the information to complete their tasks. The shared common memory 122 is itself divided into several partitions. One partition 124 holds raw or unprocessed data received from the data acquisition control system 22, which has not yet been processed by the computer system 24; a second partition 126 holds processed data or results from various stages of computation; and a third partition 128 holds status flags, which signal the programs described herein, to begin collecting data from partition(s) 124 and/or 126. After the resident programs have finished collecting data from the shared common memory 122 and performed the processing tasks assigned to the programs, the results are copied into partition 126 and signal flags in partition 128 are changed, signaling other programs, described below, that the data in partition(s) 124 and/or 126 needed to perform their tasks is available.

The preferred embodiment of the invention utilizes five application programs, described below, that run on the main computer 112.

One of these five programs is the data acquisition and environmental control manager 130. The environmental control functions of this program 130 are disclosed in greater detail, supra. The data acquisition functions of this program 130 involve collecting data which has been sent to the computer system 24, from the data acquisition control system 22, via a high-speed communication link 26, and depositing the data in the shared common 122.

The computer also contains a coprocessor manager program 134 for supervising coprocessor 114. The main function of program 134 is to send data from partition 124 to coprocessor 114 and to bring the coprocessor's results back to be stored in partition 126. The manager program 134 for coprocessor 114 takes raw data from partition 124 of the shared common memory 122, sends it to coprocessor 114 which performs its processing task, receives the results, performs additional computations, described below, and finally copies the results into partition 126 of the shared common memory 122.

The processing tasks for coprocessor 114 and coprocessor manager program 134 are disclosed in greater detail below.

A fifth program 135 is responsible for preparing the dilatometry data collected for being graphically displayed in curve form, and then fitting a formula to represent the actual curve. Such curves and formulas can be generated for each parameter of the object measured for various geometrically regular shaped objects for various rates of temperature change, for various methods of changing the temperature, and for averages of several samples.

A display program 136 in the main computer 112 provides for a user interface with the apparatus A. This program 136 is disclosed in more detail hereinafter.

The data archive program 138 electronically stores, in a permanent memory device 28, selected data and results generated by the computer system 24.

These five programs do not run in any particular order; however, they can be prioritized. For example, operating safety is of primary importance; therefore, the program which monitors and controls the apparatus' environmental control equipment is given highest priority. Or, by way of another example, if collecting data over an entire temperature range is more important than displaying the information in real time, the programs necessary to collecting data take priority over the display program.

Data Acquisition and Environmental Control Manager

Considering the five programs described above in more detail, the primary function of the data acquisition and environmental control manager 130 is to receive data from the data acquisition control system 22. The program 130 begins by initializing all data acquisition counters 92 in the data acquisition control system 22. The program may shift into a standby mode and wait for the data acquisition list sequencers 102 to collect a predetermined set of raw data, for example, five sets of raw data. Once the plurality of sets of raw data has been collected, program 130 accepts the raw data and places it in partition 124 of the shared common memory 122 to make it available to the other programs previously described. The transfer of such sets of raw data at one time is not necessary, but is preferably done in order to reduce the amount of overhead time associated with transferring information into the main computer 112.

In addition to acquiring data from the source/detector apparatus 10, program 130 also collects data from pyrometers 16. The electronic signal from the pyrometer 16 is used to calculate the temperature of the tube P for each set of data from the detectors 60. The calculation is performed in the curve-fit program 135 as described below. Temperature data is acquired in a manner that allows for continuous temperature readings for the entire temperature range. Both the source/detector data and the pyrometer data are collected through the use of a fast monitoring routine in program 130, since this data must be collected at a high sampling rate. For safety reasons, readings from radiation monitors 34 are also collected using the same fast monitoring routine to assure that radiation is kept within safe limits. If radiation readings are abnormally high, this program 130 will sound an alarm 46 and, if the radiation is abnormally extreme, it will force the radiation sources 54 to shut down.

In addition to the fast monitoring data acquisition function, the data acquisition and environmental control manager 130 performs several slow monitoring functions. The slow monitoring activities include acquisition of data concerning air temperature not shown and pressure not shown inside the detector housing 14, cooling water, temperature 40, pressure 42, and cycling of mill air purge system 38. The program sounds an alarm 46 when air temperature and pressure go outside a specific range, indicating a system failure. If the temperature or pressure conditions become too dangerous, this program 130 will also shut down the entire system and activates the water quench system.

Coprocessor Manager

The purpose of the coprocessor manager 134 is to calculate outside diameter, inside diameter, and (x,y) centers of the two diameters. The program runs cyclically—initializing when the data acquisition manager 130 trips a status flag in partition 128 of the shared common memory 122 indicating that a set of raw data 124 is stored in the shared common memory 122. However, before performing these calculations, a number of other calculations must be performed. One of these calculations is to determine the length of material in the paths between the source 54 and each detector 62. This is possible because the presence of a solid object, such as tube P in the path of the gamma rays 56, attenuates the gamma ray signal 58 received by the detector 62. The greater the length of material the gamma rays 56 must travel through, the greater the attenuation of gamma rays.

The computational burden of calculating these path lengths is passed to a coprocessor 114 that is peripheral to the main computer 112. The coprocessor program 134 periodically sends one set of scaler data to the coprocessor 114, allowing the main computer 112 to perform other tasks, while the coprocessor 114 is working on calculating path lengths. To calculate the path lengths for a set of scaler data, coprocessor 114 must have access to two additional sets of scaler data: the background count rate and the air count rate. The background count rate is obtained while the radiation source 54 is closed; the air count rate is obtained while the radiation source 54 is open, with no solid objects in the gamma ray beam 56.

Before using the air count rate and the tube attenuated count rate in any calculations, these count rates must be corrected for the interval of time that the signal conditioning subassembly 18 is inhibited by the detection of a gamma ray pulse. During this time, gamma rays 56 are entering the detectors 62, but are not being counted. This short interval of time, described earlier as "dead time," is accounted for by the following formulas:

$$A_i' = A_i/[1 - A_i(T_1/T_2)]$$

$$P_i' = P_i/[1 - P_i(T_1/T_2)]$$

where "i" ranges from 1 to the maximum number of detectors 62, "$A_i$" represents the air count, "$P_i$" represents the tube attenuated count, "$T_1$" represents the time that the subassembly 18 channel 72 is inhibited after a pulse is detected, "$T_2$" represents the data acquisition time, and "$A_i'$" and "$P_i'$" represent the dead time corrected count rates "$T_1/T_2$" is typically approximately $1.5 \times 10^{-6}$ and the quantities $A_i(T_1/T_2)$ and $P_i(T_1/T_2)$ are much less than 1 in practical applications. It is normally not necessary to correct the dead time for the background count rate because the count rate is slow enough that the correction is insignificant.

After dead time corrections have been made to the air count and tube attenuated count, the background count, "$B_i$" is, subtracted from the tube attenuated count and the air count:

$$A_i'' = A_i' - B_i$$

$$P_i'' = P_i' - B_i$$

where "$A_i''$" represents the air count after being corrected for dead time, and "$P_i''$" represents the tube attenuated count after being corrected for dead time.

After the dead time and background count corrections have been completed, it is also necessary to correct for radiation that has deviated from its path and undesirably entered into a detector out of line of its original path. This radiation is called "scattered radiation." Scattered radiation is a by-product of the interaction of the gamma rays with the atoms in the tube P. The attenuation is caused by gamma rays hitting atoms in the wall of tube P and being absorbed or scattered. Unfortunately, some of the scattered radiation is picked up by detectors 62, not originally in the line of the radiation 56 as it leaves the source. The detector 62 readings must be corrected to account for the proportion of the count caused by scattered radiation rather than direct emissions. However, before completing this task, the air count and pipe count data must be normalized as if each had a constant flux of radiation. The reason this is required is that each detector 62 has uncontrollable differences in radiation detection efficiencies which must be normalized when considering the count rate corrections in a detector based on the count rate in neighboring detectors. The normalized air count rates, $A_i'''$, and pipe count rates, $P_i'''$, are:

$$A_i''' = C/D_i^2$$

$$P_i''' = P_i''[A_i'''/A_i'']$$

where "C" is a totally arbitrary constant, "$D_i$" is the source to detector distance, "$A_i'''$" and "$P_i'''$" are the dead time corrected, background subtracted air and pipe count rates, respectively. The "$D_i^2$" term corrects the constant radiation flux rate for differences in distance between the sources and each detector.

After the tube attenuated count rate has been normalized, corrections can be made for radiation scattering caused by the detectors 62 themselves, rather than the tube P. This type of scattering is commonly called "interdetector secondary scattering." Corrections for interdetector secondary scattering are accounted for by:

$$P_i'''' = P_i''' - \Sigma_j[N_j(P_{i+j}''' + P_{i+j}''')]$$

where "J" and the "$N_j$" are determined empirically from calibration measurements.

A final correction to the count rate is attributed to radiation scattering from the pipe itself and other supporting construction materials. This correction is proportional to the count rate and does not consider variations from detector to detector. The fully corrected count rates are then:

$$P_i''''' = P_i'''' - BA_i'''$$

where "B" is determined empirically from calibration measurements.

Path lengths are now calculated using "$P_i'''''$" and "$A_i'''$" through the formula:

$$L_i = F \ln(A_i'''''/P_i''''')$$

where the value of "F" is related to the X-ray absorptivity, "$\mu$" and density, "p", by $$F = (1/\mu p)$$

The X-ray absorptivity is dependent upon the X-ray energy and pipe chemical composition. The pipe material density, p, depends upon the chemical composition and temperature.

Finally, the path lengths are corrected to account for the nonlinearity of path lengths from one detector 62 to the next. This is done with the following quadratic formula:ps
$$L_i' = X_i + (Y_i)(L_i) + (Z_i)(L_i)^2$$

where "$L_i'$" is the corrected length, "$L_i$" is the uncorrected length and "$X_i$", "$Y_i$" and "$Z_i$" are factors which were determined by the calibration software described below.

In addition to calculating path lengths, coprocessor 114 also performs a data reduction task to determine which data points will be used to calculate the outside diameter and inside diameter of the tube P and then corrects the data points for an aperture size as described below.

The data is reduced through the use of the following analysis. The three detector arrays 60 see a shadow of the tube P of varying intensity. This shadow is commonly called the tube profile. There is a sharp difference where the shadow begins on the detector array 60. Continuing along the length of the detector array 60, the shadow becomes progressively darker. The shadow becomes distinctly lighter again where the inner diameter of the tube P begins. From the point where the inside diameter begins until the center of the tube P, the shadow becomes progressively lighter. After the center of the tube, the shadow becomes darker until it become distinctly darker where the inner diameter ends. At the point the inner diameter ends, the shadow becomes progressively lighter until the shadow abruptly ends. These distinct changes in the shadow are used to determine the inside and outside diameters of the tube P.

However, prior to performing these calculations, the data points must be corrected for aperture size by indexing a table containing values appropriate for the specified size of tube P that is being produced. In this way, the number of and distance between the path length data points which will be used in further calculations is determined.

Since the edges of the inside diameter may not correspond to the index set by the outside diameter indexing determination above, the index to be used to calculate the inside diameter is offset from the starting outside diameter index by the following formula:

$$\text{Index} = \text{INTEGER } (C_1 + (\text{wall}) (C_2))$$

where "$C_1$" and "$C_2$" are constants.

Figure 8:
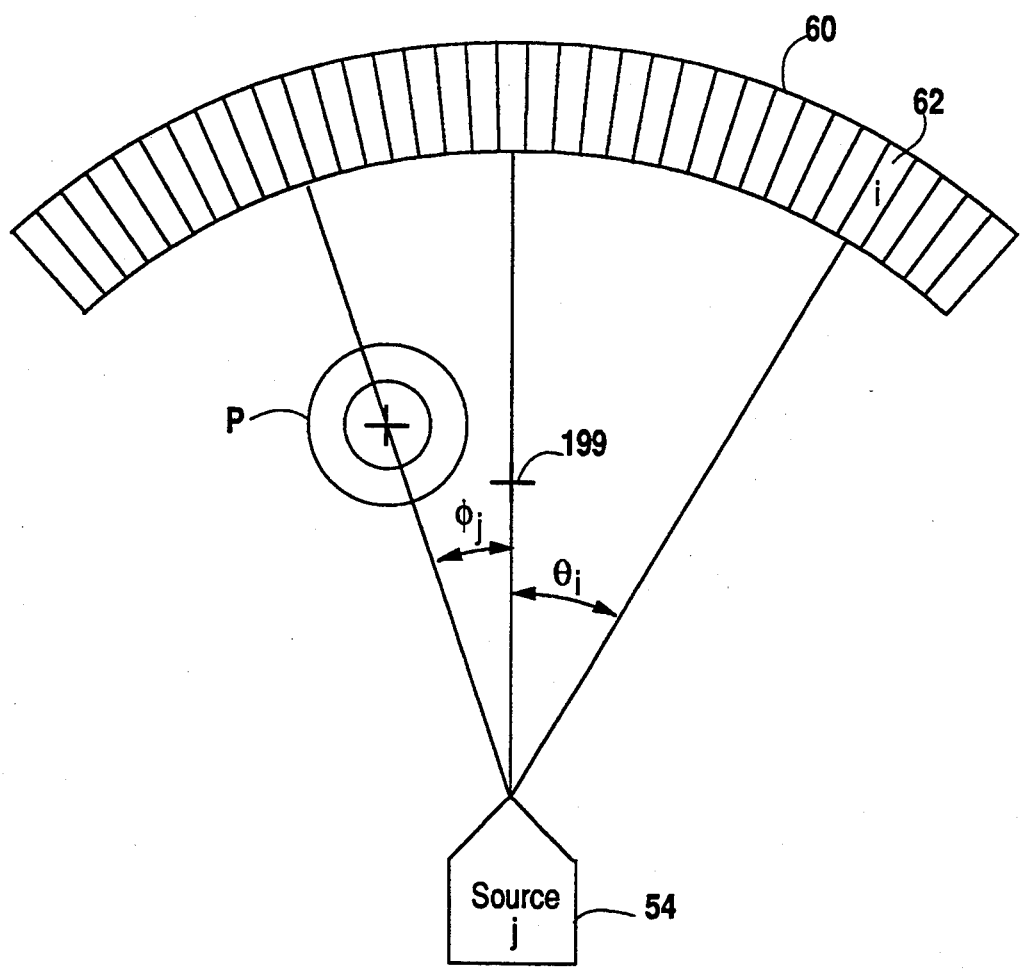
FIG. 8 is a simplified diagrammatic representation showing parameters used in the calculation algorithms.
Figure 9:
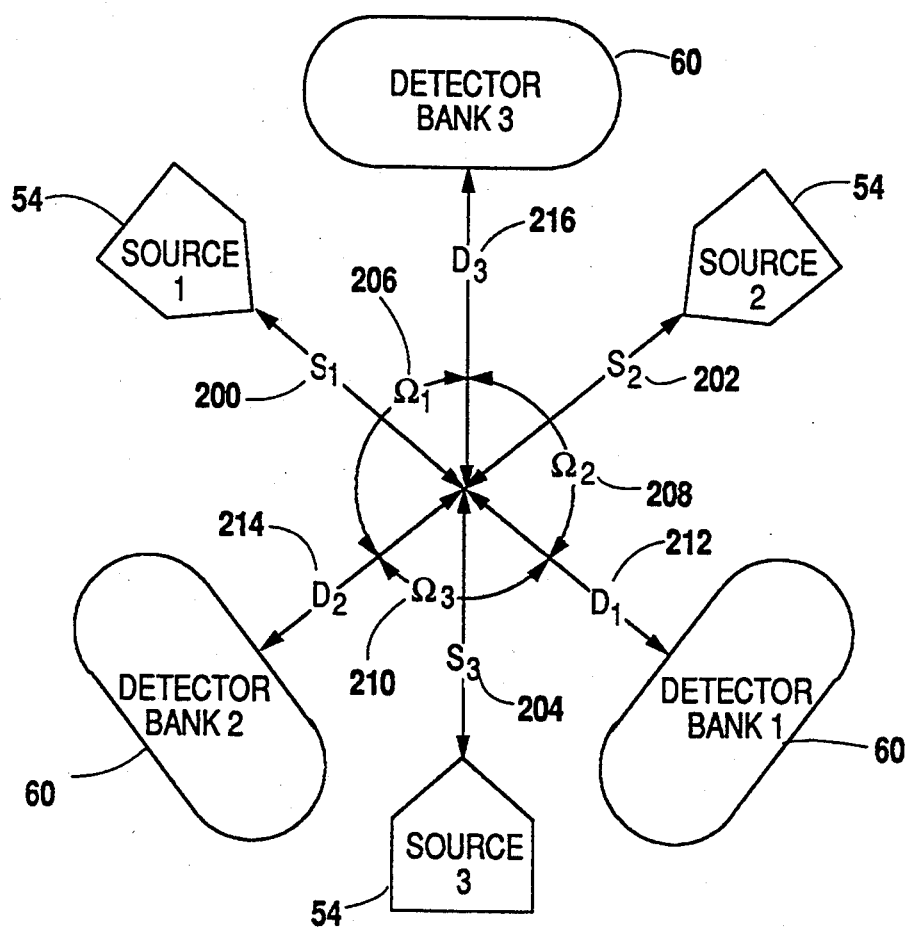
FIG. 9 is a simplified diagrammatic representation of the parameters used by the computer system to calibrate the apparatus to account for the geometry of the source/detector apparatus.

The outside diameter and inside diameter calculations are executed by the coprocessor manager program 134 in the main computer 112. The first calculation executed is to determine the angle to the tube P center, as seen by each of the three detector arrays 60. The calculation executed $$\phi_j = \frac{1}{2} L_i^{-1} \frac{2A_1A_5 - A_2A_4}{2A_3A_4 - A_2A_5}$$

where "$\phi_j$" represents the angle between a line 199 drawn from the center of the detectors 60 to the source 54 and the tube P center (see FIG. 8), "j" ranges from 1 to 3 (one for each detector array 60), "$L_i$" represents the path length as measured by the ith detector 62, and $$A1 = \tfrac{1}{2}[\Sigma_i \cos^2\Theta_i - 1/N(\Sigma_i \cos2\Theta_i)^2]$$

$$A2 = \Sigma_i \sin2\Theta_i \cos2\Theta_i - 1/N(\Sigma_i \sin2\Theta_i)(\Sigma_i \cos2\Theta_i)$$

$$A3 = \tfrac{1}{2}[\Sigma_i \sin^2\Theta_i - 1/N(\Sigma_i \sin2\Theta_i)^2]$$

$$A4 = \Sigma_i (L_i/2)^2 \cos2\Theta_i - 1/N[\Sigma_i(L_i/2)^2 \cos2\Theta_i]$$

$$A5 = \Sigma_i (L_i/2)^2 \sin2\Theta_i - 1/N[\Sigma_i(L_i/2)^2 \sin2\Theta_i]$$

where the summation extends over the four paths lengths, two on each side of the tube P, and "$\Theta_i$" represents the angle of the $i^{th}$ detector 62. See FIG. 8. Knowing the angle to the center of the tube P, as seen from each of the three detector arrays 60, it is possible to calculate the (x,y) center by triangulation between any pair of angles using the following formulas:

$$x_j = S_j \cos\Omega_j - D \cos(\phi_j + \Omega_j)$$

$$Y_j = S_j \sin\Omega_j - D \sin(\phi_j + \Omega_j)$$

where ($x_j$, $Y_j$) is the tube P center location as determined apparatus center to source j 54, "$\Omega_j$" is the angle to source j 54, $S_j$ is the distance from the center of the apparatus to the $j^{th}$ source 200, 202, 204, and $D_j$ is the distance 212, 214, 216 from the center of the apparatus to the center of the $j^{th}$ detector bank (FIG. 9), and:

$$D = \frac{DL + DP}{DD}$$

where $DL = -\cos(\phi_{j+1} + \Omega_{j+1})(S_{j+1}\sin\Omega_{j+1} - S_j\sin\Omega_j)$ $DP = -\sin(\phi_{j+1} + \Omega_{j+1})(S_{j+1}\cos\Omega_{j+1} - S_j\cos\Omega_j)$ $DD = -\sin(\phi_j + \Omega_j)\cos(\phi_{j+1} + \Omega_{j+1}) - \cos(\phi_j + \Omega_j)\sin(\phi_{j+1} + \Omega_{j+1})$ After the above calculations have been completed, the outside diameter as seen by each detector array 60, "j", can be calculated as follows:

$O.D._j = 2DC_j[(TUL_j - TUR_j)/DEN_j]^{\frac{1}{2}}$ where $DC_j = [(S_j\cos\Omega_j - x_j)2 + (S_j\sin\Omega_j - Y_j)^2]^{\frac{1}{2}}$ $TUL_j = \Sigma_i(L_i/2)^2\{3N - 4[(\cos2\phi_j \Sigma_i \cos2\Theta_i) + (\sin2\phi_j \Sigma_i \sin2\Theta_i)]$
$(\cos4\phi_j \Sigma_i \cos4\Theta_i) + (\sin2\phi_j \Sigma_i \sin2\Theta_i)$ $TUR_j = 2F_1F_2$ $DEN_j = 4[\Sigma_i(L_i/2)^2 F_{2j} - NF_{1j}]$ and $F1_j = \Sigma_i(L_i/2)^2 - (\cos2\phi_j \Sigma_i(L_i/2)^2 \cos2\phi_i) - (\sin2\phi_j\Sigma_i(L_i/2)^2 \sin2\phi_i)$
$F2_j = N - (\cos2\phi_j\Sigma\cos2\phi_i) - (\sin2\phi_j\Sigma_i\sin2\phi_i)$ Knowing the outside diameter enables a prediction of the shadow or path lengths that would be caused by a solid bar with the same outside diameter. The measured path lengths are subtracted from the solid bar path lengths and the inner circle (x, y) center and the inside diameter are determined in the same manner as the outer circle center and the outside diameter were determined, supra.

Curve-Fitting Program

A curve-fitting program 135 performs two primary functions in the invention: it plots the data points collected and generates a curve that best matches the data, and it generates a formula that represents the best curve fit or match. Convention algorithms are adequate to perform both of these functions.

Display Manger

A display program 136 provides user interface to the apparatus (FIG. 7). Through the display program 136, the user has the ability to: 1) enter object specification and metallurgical chemistry data, 2) control the apparatus' operation, 3) review the measurement data in tabular form, 4) visually view data in graphic form, and 5) monitor the environmental and safety conditions of the apparatus while in operation. The display program 136 is preferably menu driven to give the user easy access to information and the system control commands available to him.

The user is provided with means to enter object specifications such as: cross-sectional shape and material composition of the object. The display program 136 will take this information to the shared common memory 122 in the main computer 112 for other programs to access.

The display program 136 provides for means to: 1) terminate and initiate processing of data, open and close the radiation sources 54, 2) adjust the sampling rate, and 3) set parsing interval spacing for data reduction in the coprocessor 114.

Several options are available for displaying the information generated by the apparatus A. It can be displayed either visually or on hard copy. For example, temperature versus any outside diameter. The output can be either tabular or graphic. Dilatometry curves, showing temperature versus dimensions, can be graphically constructed and displayed on the video screen or on hard copy. This program also provides the option to later view or produce hard copy of data reports or data summaries.

Data Archive Manager

The data archive program 138 stores information in disk files and provides information for operator output. The program is activated when data collection is completed by the data acquisition program 130. The display program 136 also provides output to the operator in the form of printed information or graphic displays on either the computer display screen or through a printer.

The preferred embodiment of the invention was originally intended to be used in a tube production process, which provides a sufficient time interval between testing of a sample from the batch and initialization of production to permit the main computer 112 to perform these calculations. If necessary, these calculations could be dedicated to additional coprocessors, if this time interval was eliminated. The invention's structure allows for a great deal of flexibility to adapt to different production processes in order to maximize efficiency and minimize equipment cost.

Calibration

In addition to the programs described above, the disclosed embodiment includes a calibration program. Calibrating the apparatus A is essential to obtaining accurate results. The calibration program for this particular embodiment performs two separate and independent calibrations: one calibration determines apparatus A geometry parameters of the source/detector apparatus 10, and the other calibration determines the path length quadratic correction parameters for each detector 62.

Since the preferred embodiment contains at least three source and detector array pairings 52, the geometry of the source/detector apparatus 10 is defined in ten parameters which are all measured from the source/detector apparatus' center: three parameters define the distances 200, 202 and 204 of each source 54 from the center, three parameters define the angles 206, 208 and 210 between the three detector arrays 60, three parameters define the distances 212, 214 and 216 of each detector array 60 from the apparatus center, and one defines the interdetector spacing between each detector 62 in the detector array 60. Suitable source/detector parameters may be: interdetector spacing of nominally 0.278 inches, source 54 distance to center nominally 32 inches, and detector array 60 distance to center nominally 29 inches.

Figure 10:
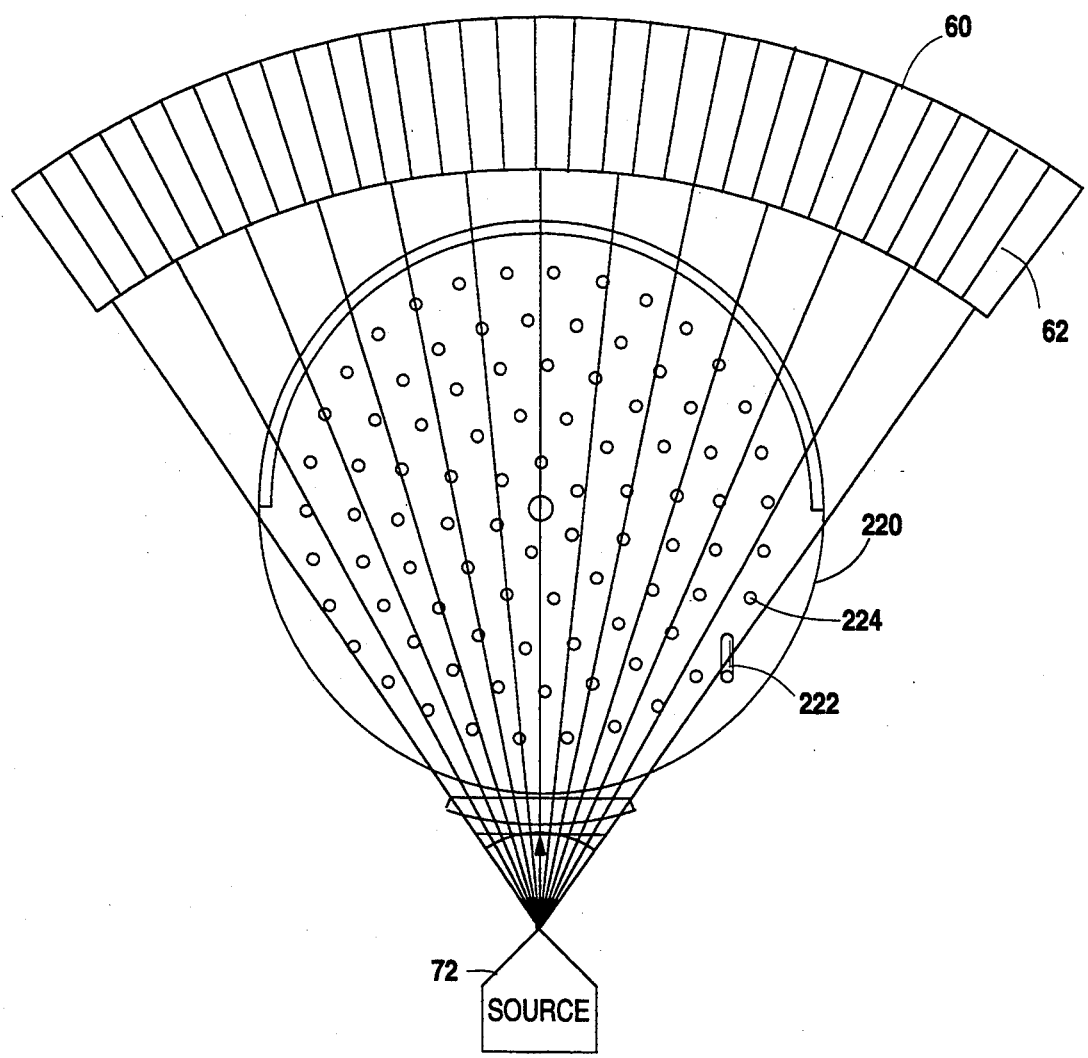
FIG. 10 is a simplified diagrammatic representation of a calibration plate in position between a source and detector array which is used to calibrate the geometrical relationship between the source and detector arrays.

The method used to determine these parameters involves a calibration plate 220 which can hold fixed in a multitude of known calibrated positions 224 a steel bar 222. See FIG. 10. The preferred embodiment utilizes a calibration plate 220/steel bar 222 design with 91 different calibrated locations 224. After a measurement has been taken by the apparatus for each of the locations, a chi-squared minimization is performed by the geometry parameter calibration program to determine the ten geometric parameters of the apparatus. This calibration is necessary because the tube P is not held in place and varies its position in the apparatus as it moves through it while being scanned.

The second calibration performed by the calibration program is designed to normalize the path length calculation from one detector 62 to another in order to have consistent results as the tube P varies from the center of the scanning apparatus. This calibration is necessary because the detectors 62 are not all equal or equally positioned vector-linearly with the gamma rays. The calibration calculation results are used to normalize the path length during calibration. The formula used to normalize the path length is the following:

$$L' = X + (Y)(L) + (Z)(L)$$

Figure 11:
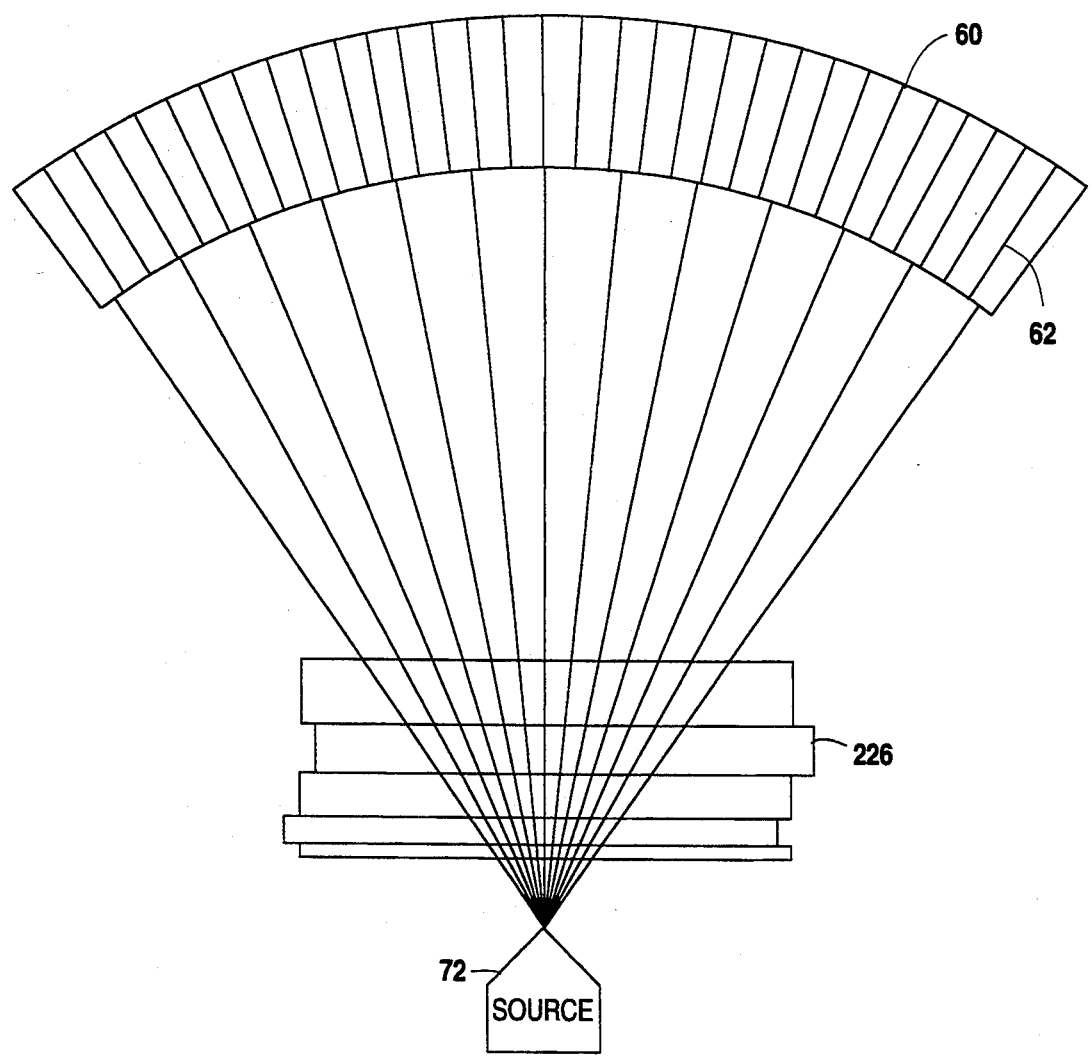
FIG. 11 is a simplified diagrammatic representation of other calibration plates of varying thickness in position between a source and detector array which are used to calibrate the individual de detector array.

Each detector 62 has a unique "X", "Y" and "Z" which is calculated and determined by the calibration program. The method used to determine these parameters involves a set of steel plates 226 that vary in thickness from 0.5 inches to 5.5 inches, in 0.5 inch increments. See FIG. 11. After unnormalized measurements are taken for each plate, a chi-squared minimization is performed to determine the normalization parameters "X", "Y" and "Z" for each detector. These parameters are used later in the coprocessor program 134 where path lengths are calculated during normal operation.

Operation

Figure 12A:
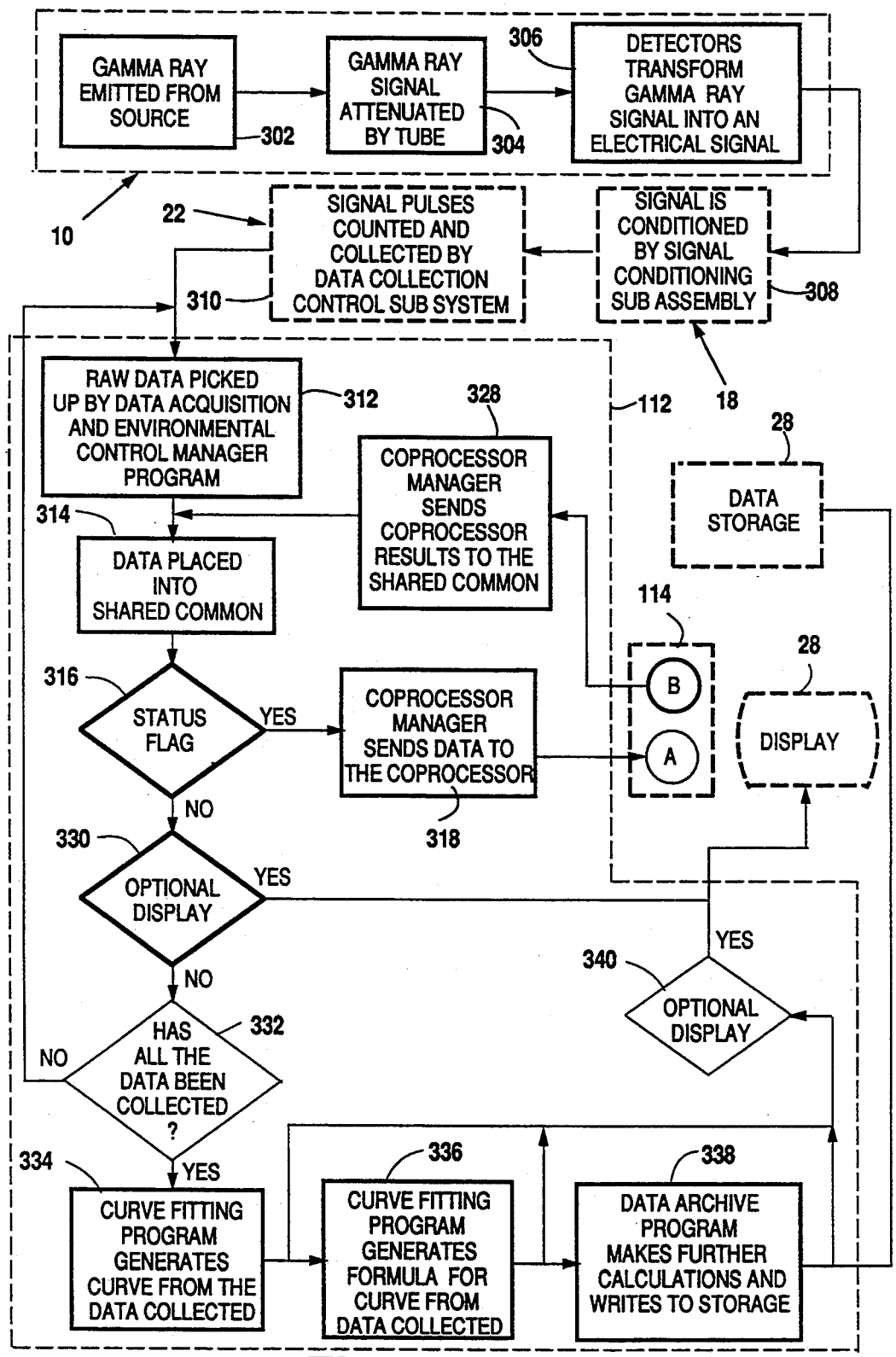
Figure 12B:
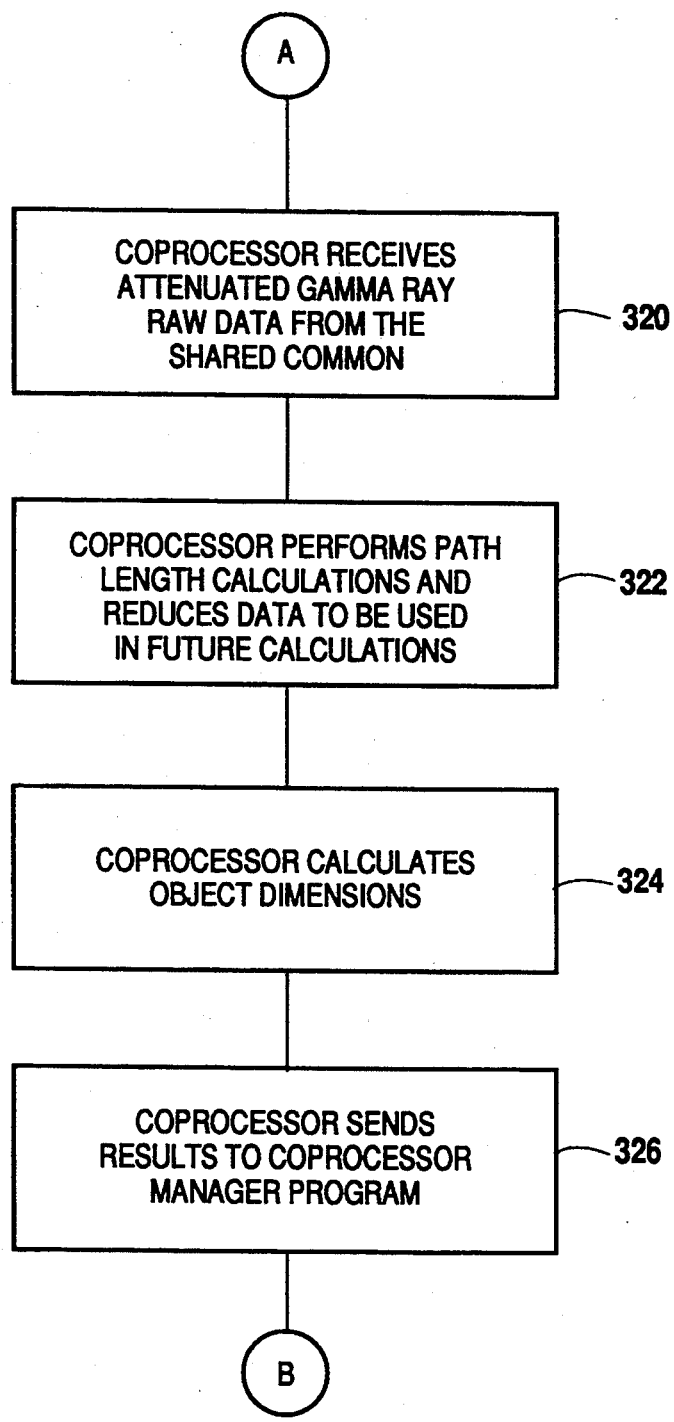

The following description of the data flow and the graphical representation of the same in FIGS. 12a and 12b is only representative. As mentioned supra, the programs described herein do not necessarily run in any particular order. In fact, they often run at the same time. For example, while the coprocessor manager 134 is calculating path lengths from the first set of cross sectional data, the data acquisition manager 130 may be collecting the second set of cross-sectional data. FIG. 12a and the following description are included in this disclosure to help teach how the disclosed apparatus works, but is not meant to suggest that the calculations are performed in this order or that the tasks are divided and assigned in this manner.

When the system is turned one, the source/detector apparatus 10 begins to emit and detect gamma ray signals in step 302. The presence of tube P in the path of the gamma rays 56 causes the gamma ray signal to be attenuated in step 304. Detectors 62 transform the gamma ray signal to electrical signals in step 306. The signals from the detectors 62 are conditioned in step 308 by the detector signal conditioning subassembly 18 and collected and counted in step 310 by the data acquisition control system 22. The data acquisition control system 22 makes sets of data available to the computer system 24 via a high speed low noise communication link 26. The data acquisition manager program 130 in the main computer 112 picks up the raw digital data in step 312 and places the data in step 314 into partition 124 of the shared common memory 122 of the main computer 112.

Five separate programs take turns monitoring the status flags 128 in the shared common memory 122 waiting to be called on to perform their tasks. These programs include: the data acquisition and environmental control program 130 the display program 136, the coprocessor manager 134, the curve-fitting program 135 and the data archive program 138. The display program 136 serves as the operator interface to the computer system 24. It can be used to access any information in either the shared common 118 or the long term memory device 116. The display program 136 can instruct this information to be displayed at the operator's option. For the sake of simplicity, this description of the data flow discussion will trace a single set of cross-sectional data.

After all the raw data 124 is collected, a status flag 128 is raised calling the coprocessor manager program 134 into action in step 316. Raw data is sent in step 318 from partition 124 to the coprocessor 114 by the coprocessor manager 134. Coprocessor 114 receives the raw data in step 320 from the shared common memory 122. See FIG. 12b. The coprocessor 114 performs path length calculations and reduces the raw data in step 322. The coprocessor 114 uses the path length calculation results to calculate outside diameter, inside diameter, wall thickness and (x,y) centers for each OD and ID measurement in step 324. Coprocessor 114 sends the results in step 326 to the data acquisition manager 130, which in turn places the results, in step 328, in partition 126 of the shared common memory 122. At this point, the operator has an option of displaying the results thus far 330.

After the computer 112 determines that the coprocessor 114 has completed processing data for the desired temperature range in step 332. In step 336 the curve fitting the curve-fitting program 135 generates a graphical representation of the data, a dilatometry curve in step 334 which can optionally be displayed on a display peripheral 28. The curve-fitting program 135 also generates a formula that represents the shape of the dilatometry curve in step 336 which can be optionally displayed, in step 340, on display peripheral 28. In step 338 the data archive program 138 calculates an average of the dilatometry information for several tests run on the same material and shape. The results from this step can be optionally display, in step 340, on display peripheral 28. The data archive program 138 stores the data, formula, and graphs in step in an electronic peripheral device 28.

The foregoing disclosure and description of the invention are illustrative and explanatory thereof, and various changes in the details may be made without departing from the spirit of the invention.

We claim:

1. A method for nondestructively determining the dimensional changes in an object as a function of temperature over a desired temperature range, comprising:
    a) scanning a single cross-section of said object with penetrating radiation along a plurality of paths;
    b) sensing the temperature of the object as the object is being scanned and generating temperature signals representative of the temperature of the cross-section of the object;
    c) generating electrical signals representative of the radiation attenuation along each of the plurality of paths through the cross-section of the object;
    d) converting the electrical signals representative of the attenuated penetrating radiation signals into signals representative of the density-length of the object along each of the plurality of paths;
    e) processing the density-length signals to determine, by use of a computer model of the object to be examined, dimensional measurements of a cross-section of the object;

f) processing the temperature signals to generate a temperature which corresponds with each determined dimensional measurement;

g) allowing the object to increase and/or decrease in temperature; and h) periodically repeating steps a) through g) at different temperatures whereby a series of correlated dimensional and temperature measurements are taken of the same cross-section over the desired temperature range.

2. The method of claim 1, which further comprises:
generating a graphical representation of temperature versus dimensional data for each dimension of the object.

3. The method of claim 1, which further comprises:
generating a model of the dimensional data as a function of temperature for each dimension of the object.

4. The method of claim 1, wherein:
the object is geometrically regular-shaped.

5. The method of claim 4, which further comprises:
generating a graphical representation of temperature versus dimensional data for each dimension of the temperature.

6. The method of claim 4, which further comprises:
generating a model of the dimensional data as a function of temperature for each dimension of the object.

7. The method of claim 4, wherein:
a) the geometrically regular-shaped object is cylindrical; and
b) the dimensions determined using the computer model include outside diameter and ovality.

8. The method of claim 7, which further comprises:
generating a graphical representation of temperature versus dimensional data for each dimension of the object.

9. The method of claim 7, which further comprises:
generating a model of the dimensional data as a function of temperature for each dimension of the object.

10. The method of claim 7, wherein:
a) the geometrically shaped object is tubular; and
b) the dimensions determined using the computer model also include inside diameter, wall thickness and eccentricity.

11. The method of claim 10, which further comprises:
generating a graphical representation of temperature versus dimensional data for each dimension of the object.

12. The method of claim 10, which further comprises:
generating a model of the dimensional data as a function of temperature for each dimension of the object.

13. An apparatus for nondestructively determining the dimensional changes in an object as a function of temperature, comprising:
a) means for periodically scanning a single cross-section of the object with penetrating radiation along a plurality of paths;
b) means for periodically measuring the temperature of the same cross-section of the object when the object is scanned with penetrating radiation;
c) means for generating electrical signals representative of the radiation attenuation along each of the plurality of paths;
d) means for converting the electrical signals representative of the attenuated penetrating radiation signals into signals representative of the density-length of the object along each of the plurality of paths;
e) a computer model of the object to be examined and processing means to determine dimensional measurements of a cross-section of the object from the density-length signals produced by the converting means; and
f) means for generating a dimension/temperature profile from the determined dimensional measurements and temperature measurements.

14. The apparatus of claim 13, which further comprises:
means for generating a graphical representation of temperature versus dimensional data for each dimension of the object.

15. The apparatus of claim 13, which further comprises:
processing means for generating a model of the dimensional data as a function of temperature for each dimension of the object.

16. A method for calibrating a process control system which bases its process control calculations on measurements made at elevated or depressed temperatures of the object produced from a specific batch of raw material:
a) preparing a sample object from the batch of material;
b) fixing the sample in place in order to periodically scan a single cross-section of the object with penetrating radiation along a plurality of paths;
c) sensing the temperature of the cross-section of the object and generating temperature signals representative of the temperature of the cross-section of the object;
d) generating electrical signals representative of the radiation attenuation along each of the plurality of paths;
e) converting the electrical signals representative attenuated penetrating radiation signals into signals representative of the density-length of the object along each of the plurality of paths;
f) processing the density-length signals to determine, by use of a computer model of the object to be examined, dimensional measurements of a cross-section of the object;
g) processing the temperature signals to generate a temperature which corresponds with each dimensional measurement;
h) allowing the object to continuously increase or decrease in temperature to the desired temperature;
i) periodically repeating steps b) through h) so as to take dimensional and temperature measurements, using the same cross-section, over the desired temperature range;
j) generating a model of the dimensional data as a function of temperature for each determined dimension of the object; and
k) transferring the generated model of the dimensional data as a function of temperature to the process control system.

17. A method of developing a model of the changes in the dimensions of an object as a function of temperature over a desired temperature range, comprising:
a) scanning a cross-section of the object with penetrating radiation;

b) sensing the temperature of the object as the object is scanned;
c) generating temperature signals representative of the sensed temperature of the cross-section of the scanned object;
d) generating signals representative of the radiation attenuation through the cross-section;
e) processing the attenuation signals by use of a computer model of the object examined to determine the dimensional measurements of the cross-section;
f) correlating the temperature signals generated during a scan with the dimensional measurements generated from the attenuation signals associated with the scan;
g) allowing the object's temperature to change;
h) repeating steps a) through f) as the temperature of the object changes in order to generate dimensional measurements and associated temperature signals for the safe cross-section of the object at a plurality of temperatures; and
i) storing the object's dimensions as a function of temperature over the desired temperature range.

* * * * *